United States Patent [19]
Zakaryan et al.

[11] Patent Number: 5,183,916
[45] Date of Patent: Feb. 2, 1993

[54] PROCESS FOR PRODUCING TRI-N-BUTYLPHOSPHOROTRITHIOITE

[75] Inventors: Ara H. Zakaryan; Peter E. Newallis; Mark A. Tice, all of Leawood, Kans.

[73] Assignee: Miles Inc., Pittsburgh, Pa.

[21] Appl. No.: 339,043

[22] Filed: Apr. 14, 1989

[51] Int. Cl.$^5$ .................................. C07F 9/06
[52] U.S. Cl. ........................................ 558/95
[58] Field of Search ............................ 558/95

[56]  References Cited
U.S. PATENT DOCUMENTS

| | | | |
|---|---|---|---|
| 2,682,554 | 6/1954 | Crouch et al. | 558/92 |
| 2,943,107 | 6/1960 | Rattenbury et al. | 558/92 |
| 3,885,002 | 5/1975 | Barber | 558/95 |

OTHER PUBLICATIONS

Turner, Steph, Ph.D., B. Sc., *The Design of Organic Synthesis*, 1976 p. 149.

Primary Examiner—Nicholas S. Rizzo
Assistant Examiner—Jyothsna Venkat
Attorney, Agent, or Firm—Joseph C. Gil; Lyndanne M. Whalen

[57] ABSTRACT

Tri-n-butylphosphorothioite is produced on a continuous or semi-continuous by simultaneously adding phosphorus trichloride and butylmercaptan to a reaction vessel at a rate such that an excess of butylmercaptan is present and allowing the resultant mixture to react at a temperature of from about 120° C. to about 150° C. One or more reactors may be employed. This process is particularly advantageous for safety reasons and produces high quality phosphite which may be oxidized without purification to produce S,S,S-tri-n-butylphosphorotrithioate.

10 Claims, No Drawings

PROCESS FOR PRODUCING TRI-N-BUTYLPHOSPHOROTRITHIOITE

BACKGROUND FOR THE INVENTION

The present invention relates to an improved process for producing high quality tri-n-butylphosphorotrithioite (phosphite).

Phosphite is the intermediate from which S,S,S-tri-n-butylphosphorotrithioate (useful as a cotton defoliant) is produced. Phosphite has generally been produced by reacting phosphorous trichloride with a substantial excess of butylmercaptan. U.S. Pat. No. 2,682,554, for example, teaches the use of at least 4 mols and preferably 5 mols of butylmercaptan for each mol of phosphorous trichloride. These prior art processes are undesirable because they make it necessary to remove substantial amounts of mercaptan before proceeding with production of the pesticide S,S,S-tributylphosphorotrithioate. Such removal increases production time and is usually incomplete, resulting in a product with undesirably high levels of odorous impurities. These impurities are transferred to the product giving the pesticide an unpleasant odor.

U.S. Pat. No. 2,943,107 teaches that these difficulties may be reduced by decreasing the excess of butylmercaptan from 4 mols to 3 to 3.3 mols per mol of phosphorous trichloride. The butylmercaptan is reacted with phosphorous trichloride until the reaction has reached 85-99% completion. An oxidizing agent is then added to oxidize the phosphite to the desired product. The oxidizing agent described as preferred is air. However, the highly odorous dibutyldisulfide is one of the by-products formed from the unreacted butylmercaptan present in the reaction mixture oxidized by air.

In one attempt to overcome these odor problems, phosphorous trichloride and a slight excess (i.e., 5%) of butylmercaptan were reacted in an inert atmosphere. The hydrogen chloride which formed during this reaction was subsequently removed by a nitrogen purge at elevated temperature. The phosphite thus prepared was oxidized with hydrogen peroxide at a moderate temperature and then stripped with steam to remove the volatiles.

Each of the processes discussed above has the disadvantage of requiring the presence of large quantities of hazardous phosphorous trichloride be present in the reactor initially. Expensive equipment capable of withstanding a highly corrosive atmosphere, extensive safety measures and safety equipment were required to produce phosphite by these known processes.

It would be advantageous to have a process for producing phosphite which did not involve the presence of large quantities of phosphorous trichloride in the reaction at any stage of the process for safety considerations and which also did not produce an odorous product.

SUMMARY OF THE INVENTION

It is an object of the present invention to provide an improved process for the production of phosphite.

It is also an object of the present invention to provide a process for producing phosphite having a reduced level of impurities.

It is a further object of the present invention to provide a process for producing phosphite which minimizes the amount of phosphorous trichloride present at all stages of the process.

It is yet another object of the present invention to provide a safer process for the production of phosphite by eliminating the presence of large amounts of phosphorous trichloride in the reactor(s).

It is yet another object of the present invention to provide a process for producing phosphite having reduced levels of residual butylmercaptan on a continuous or semi-continuous basis.

These and other objects which will be apparent to those skilled in the art are accomplished by simultaneously adding phosphorous trichloride and an excess of butylmercaptan to a reaction vessel (preferably, a vessel in which at least a minor amount of phosphite is already present) and reacting those materials to form phosphite having substantially reduced levels of residual butylmercaptan. This phosphite may then be oxidized to produce the desired phosphate. In a preferred embodiment, the phosphorous trichloride and butylmercaptan are simultaneously introduced into a reactor and the reaction is completed in the same reactor. Alternatively, the phosphorous trichloride and butylmercaptan may be introduced into a first of a series of at least two reactors simultaneously. The reaction mixture may subsequently be transferred to one or more other reactors in r which the production of phosphite is completed. The vessel into which the reactants is introduced is generally maintained at a temperature of from 60° C. to 80° C. during the introduction of those materials. The temperature of the reactants is subsequently raised to a temperature of up to 150° C. during the reaction. The reactor containing the reaction mixture is purged with an inert gas such as nitrogen or helium to drive the reaction to completion.

DETAILED DESCRIPTION OF THE INVENTION

The reaction of phosphorous trichloride with butylmercaptan proceeds in three stages. In the first stage, the monobutyl substituted ester is formed. In the second stage, the dibutyl substituted ester forms. This second stage proceeds at a much slower rate than the first. In the third stage where the tributyl substituted ester forms, an equilibrium between the diester, phosphorous trichloride and mercaptan reactants and the desired trisubstituted ester exists at the point where conversion to phosphite is about 85% complete. Because each of these stages occurs at a different rate, it has been believed that undesirably long reaction times would be required if substantial excesses of mercaptan were not employed. Applicants have found, however, that the simultaneous addition of the phosphorous trichloride and butylmercaptan and the use of a nitrogen purge to remove hydrogen hcloride generated during the reaction allows the use of only a slight excess of butylmercaptan and produces phosphite in high yields with low levels of impurities or unwanted by-products.

A major advantage of the process of the present invention is its ability to produce phosphite on a continuous or semi-continuous basis with a higher degree of safety than the processes taught in the prior art. This may be accomplished by metering the continuous, simultaneous addition of both reactants to the reaction vessel so that at any time moderate excess (i.e. mercaptan of up to 100%, preferably an excess of from 2 to 30% and more preferably an excess of from 2 to 1%) is present in the reaction vessel.

When the process of the present invention is carried out on a semi-continuous basis, one or more than one reactors may be used. It is preferred that one reactor be employed in a semi-continuous procedure.

In a semi-continuous process, the temperature of the reactor is maintained at a temperature of from about 60° C. to about 80° C. during the addition of phosphorous trichloride and butylmercaptan. Addition of the reactants is discontinued when the appropriate level in the reactor or reactors has been reached. If only one reactor is being used, the temperature of that reactor is increased to a temperature of from about 120° C. to about 150° C. upon discontinuous of the addition of reactants and the temperature is maintained at this level for up to about 12 hours, preferably for about three to six hours. Upon completion of the reaction, the reactor is purged with an inert gas such as nitrogen or helium and the product phosphite may be recovered.

If two reactors are used to carry out the process of the present invention on a semi-continuous basis, the phosphorous trichloride and butylmercaptan are simultaneously introduced into the first reactor which is maintained at a temperature of from about 60° C. to about 80° C. The contents of this first reactor may be allowed to overflow into the second reactor which is maintained at a temperature of from 60° C. to 150° C. where the reaction is completed. If necessary, the temperature of this second reactor may be raised to drive the reaction forward (e.g., where the second reactor is maintained at a temperature below 120° C. during the addition of the reaction mixture thereto). The reactor is preferably purged with an inert gas such as nitrogen or helium during the reaction and upon completion of the reaction before the product phosphite is recovered.

The reactants may be added to the first reactor at a rate such that the average residence time in the system is from about 3 to about 12 hours. It is also possible but not preferable to add phosphorus trichloride and/or butylmercaptan simultaneously to any of the reactors (in addition to the first) of a cascade system.

In a continuous process, at least two and possibly three or more reactors may be employed. These reactors are preferably arranged in a cascade. In a continuous process, the phosphorous trichloride and butylmercaptan are introduced into a first reactor on a continuous basis at rates such that a moderate excess of mercaptan will always be present. It is preferred that the reactants be introduced into the first of the reactors in the cascade at a rate such that the average residence time in the entire system is from about 3 to about 12 hours.

If the first reactor is the first in a cascade of reactors, the contents of the first reactor are allowed to flow into a second reactor in the cascade which reactor may be maintained at a temperature which is above that of the first reactor but does not exceed 150° C. The residence tiem of the reaction mixture in this second reactor will depend upon the temperature of that reactor and the number of subsequent reactors in the cascade, if any.

In a preferred embodiment of the present invention, phosphite is produced on a continuous basis using three reactors arranged in a cascade. The first reactor is maintained at a temperature of from about 60° C. to about 80° C. The reactants are added to this first reactor at a rate such that the average residence time in the system of reactors is from about 3 to about 12 hours. The second reactor is preferably maintained at a temperature of from about 70° C. to about 150° C. The third reactor is maintained at a temperature which is at least as high as the temperature of the second reactor and preferably at a temperature of at least 120° C. Each reactor is preferably purged with an inert gas during the reaction to remove hydrogen chloride o generated during that reaction. Hydrogen chloride may also be removed by vacuum. After the reaction has been completed and the third or last reactor has been purged with an inert gas such as nitrogen or helium, the phosphite may be recovered from the mixture in that third or last reactor without the need for complicated purification procedures. Control of the rate of addition of the reactants to the first reactor and maintenance of the various reactors at the appropriate temperatures make it possible to control the residence times in the various reactors without interrupting the process.

It has been found that inclusion of a relatively small amount of phosphite in the reactor into which the phosphorous trichloride and butylmercaptan are simultaneously introduced before introduction of those reactants is begun is advantageous for practical reasons but is not critical to achieving the s results of the present invention.

Phosphite produced in accordance with the present invention is generally obtained In yields ranging from 85 to 98% and may be oxidized directly to form the corresponding phosphorotrithioate without the need for extensive purification. Since the phosphorous trichloride and butylmercaptan are added simultaneously and the first step of the reaction occurs readily at the temperatures of this process, only low levels of phosphorous trichloride are present at any stage of the reaction. This reduces hazards associated with phosphorous trichloride such as reactions with water, etc. (See,e.g., N. Irving Sax, Dangerous Properties of Industrial Materials, 5th Ed., Van Nostrand Reinhold Co., New York, N.Y., 1979, pg. 913.)

Having thus described our invention, the following examples are given as being illustrative thereof. All parts and percentages given therein are parts by weight or percentages by weight, unless otherwise indicated.

EXAMPLES

Example 1

The apparatus employed in this example was a single 1000 ml 4-neck flask equipped with a stirrer, a Y-adaptor with a thermometer and a condenser, a Y-adaptor equipped with a 125 ml funnel and nitrogen inlet, and a 500 ml funnel. This flask was purged with nitrogen to remove the air present therein. Thirty grams of phosphite heel (i.e., the residue from a previous phosphite-forming reaction containing a small amount of phosphite) were introduced into the reactor and the reactor temperature was raised to 70° C. The butylmercaptan was added at a rate of 2.83 ml/min and the phosphorous trichloride was added simultaneously at a rate of 0.74 ml/min. for two hours. The temperature was maintained at 70° C. during the entire addition period. The temperature in the reactor was then increased to 115° C. and maintained at that temperature for seven hours. The reaction mixture was periodically cooled, the reactor was purged with nitrogen and samples were taken and analyzed by gas chromatography to determine the extent of completion of the reaction.

310.3 grams of phosphite were obtained and 14.2 grams of unreacted butylmercaptan were recovered.

Example 2

Example 1 was repeated with the exception that the temperature during the simultaneous addition of the reactants was maintained at 80° C. during the addition and that the reaction mixture was heated for 3 hours at 115° C. before the first sample was taken. The mixture was reheated to 130° C. for 30 minutes after sampling. After stripping off the HCl generated during the reaction, unwanted by-products and unreacted materials, 319.8 grams of phosphite were obtained.

Example 3

The procedure of Example 1 was repeated using the same reactants in the same quantities. The temperature at which the reactor was maintained during the simultaneous addition of those reactants was reduced to 60° C. The first sample was taken after the reaction mixture had been heated for three hours at 115° C. The reaction mixture was then heated to 130° C. for 30 minutes. 317 grams of phosphite in which the odor of butylmercaptan could not be detected were obtained.

Example 4

Two reaction vessels were used to carry out the process of the present invention on a continuous basis. The first reactor was a modified 500 ml flask having an overflow tube to the second reaction vessel. The second reactor was a 1000 ml 4-necked flask.

Butylmercaptan was added at a rate of 6.25 ml/min. to the first reactor containing phosphite heel in which 30 grams of o phosphite were present which reactor was maintained at a temperature of approximately 80° C. Phosphorous trichloride was simultaneously added to the same reactor at a rate of 1.38 ml/min. The residence time in the first vessel was 60 minutes before the contents of the first vessel were transferred to the second vessel which had been preheated to 132° C. The contents of the second reactor were heated at 132° C. for three hours to ensure completion of the reaction. It would, however, be possible to control the addition of reactants to maintain a rate such that the reaction in the second vessel would be completed in a longer or a shorter period of time. Upon completion of the reaction in the second reactor, 271 grams of phosphite in which the odor of butylmercaptan could not be detected were obtained.

Example 5

The process of the present invention was carried out using three reactors arranged in a cascade. The first and second vessels were 500 ml 4-necked flasks modified with an overflow tube. The third reactor was a 1000 ml 4-necked flask.

The butylmercaptan was added at a rate of 6.08 ml/min to the first reactor which already contained a phosphite heel. s Simultaneously, the phosphorous trichloride was added at a rate of 1.46 ml/min into the same reactor. The reactor temperature was maintained at 80° C.-83° C. during the addition of the reactants.

The contents of the first reactor were allowed to flow into the second reactor at 127° C. and into the third reactor at 130° C. The average total residence time was 5.5 hours. Phosphite in which the odor of unreacted butylmercaptan could not be detected was obtained in a yield of 95.2%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of tri-n-butyl-phosphorotrithioite on a continuous or semi-continuous basis comprising
    a) simultaneously introducing phosphorous trichloride and butylmercaptan into a reaction vessel which is maintained at a temperature of from about 60° to about 80° C.,
    b) heating the mixture of a) to form tri-n-butylphosphotrithioite in a relatively substantial amount and,
    c) recovering tri-n-butylphosphorotrithioite.

2. The process of claim 1 in which the butylmercaptan is added in a manner such that it is always present in a stoichiometric excess of from 0-100%.

3. The process of claim 1 in which at least two reaction vessels are employed.

4. The process of claim 3 in which the reaction vessels are arranged in a cascade.

5. The process of claim 4 in which the phosphorous trichloride and butylmercaptan are introduced simultaneously into a first reaction vessel maintained at a temperature of from 70° C.-85° C. during the addition and the contents of the reaction vessel are allowed to overflow into a second reaction vessel where they are further reacted.

6. The process of claim 5 in which the contents of the second reaction vessel are allowed to overflow into a third reaction vessel in which the reaction of butylmercaptan is substantially completed.

7. The process of claim 1 in which the reaction vessel is heated to a temperature of from about 120° C. to about 150° C. upon completion of the addition of phosphorous trichloride and butylmercaptan.

8. The process of claim 1 in which the vessel from which the tri-n-butylphosphorothioite is recovered is purged with nitrogen before the tri-n-butylphosphorothioite is recovered.

9. The process of claim 1 in which hydrogen chloride generated during b) is removed from the reaction vessel by vacuum.

10. The process of claim 1 in which the butylmercaptan is added in a manner such that it is always present in an excess of from 2 to 25%.

* * * * *